US012667084B2

(12) United States Patent
Nahm et al.

(10) Patent No.: US 12,667,084 B2
(45) Date of Patent: Jun. 30, 2026

(54) SYSTEM FOR EARLY DETECTION OF INFECTIOUS DISEASES IN POULTRY

(71) Applicant: KONKUK UNIVERSITY INDUSTRIAL COOPERATION CORP., Seoul (KR)

(72) Inventors: Sang-Soep Nahm, Seoul (KR); Kyu Jik Kim, Daejeon (KR); Jinyong Noh, Gyeonggi-do (KR)

(73) Assignee: KONKUK UNIVERSITY INDUSTRIAL COOPERATION CORP., Seoul (KR)

( * ) Notice: Subject to any disclaimer, the term of this patent is extended or adjusted under 35 U.S.C. 154(b) by 409 days.

(21) Appl. No.: 18/033,234

(22) PCT Filed: Oct. 12, 2021

(86) PCT No.: PCT/KR2021/013984

§ 371 (c)(1),
(2) Date: Apr. 21, 2023

(87) PCT Pub. No.: WO2022/086014

PCT Pub. Date: Apr. 28, 2022

(65) Prior Publication Data

US 2023/0389525 A1     Dec. 7, 2023

(30) Foreign Application Priority Data

Oct. 22, 2020    (KR) ........................ 10-2020-0137664

(51) Int. Cl.
*A01K 45/00*        (2006.01)
*A01K 29/00*        (2006.01)
(Continued)

(52) U.S. Cl.
CPC ............ *A01K 45/00* (2013.01); *A01K 29/005* (2013.01); *G01J 5/0025* (2013.01); *G16H 50/80* (2018.01); *G01J 2005/0077* (2013.01)

(58) Field of Classification Search
CPC ........ A01K 31/00; A01K 45/00; A01K 31/22; A01K 29/005; A01K 29/00; G16H 50/80;
(Continued)

(56) References Cited

U.S. PATENT DOCUMENTS

2010/0198024 A1*   8/2010   Elazari-Volcani ..... G16H 10/60
                                                                    128/903
2013/0006065 A1     1/2013   Yanai
(Continued)

FOREIGN PATENT DOCUMENTS

KR         101894635      8/2018
KR         101961311      3/2019
(Continued)

*Primary Examiner* — Peter J Macchiarolo
*Assistant Examiner* — Mireille S Sadate-Moualeu
(74) *Attorney, Agent, or Firm* — DUANE MORRIS LLP; Gregory M. Lefkowitz; Brandon A. Chan

(57) ABSTRACT

The present disclosure relates to a system for measuring changes in the vital signs of poultry and a method for predicting whether poultry is infected with pathogens using the same. The present disclosure can be helpfully used to determine an overall health condition including the outbreak of various poultry diseases by measuring quantitative changes in vital signs of poultry in real time. In particular, the present disclosure provides reliable real-time information about changes in vital signs through comparison of body temperature and noise measurement values of poultry for each time period reflecting circadian changes of the poultry, rather than simple comparison of the body temperature and noise measurement values with simple reference values, and thus can be used for early diagnosis of highly infectious pathogens such as avian influenza virus and early isolation of confirmed cases, and ultimately for effective prevention of the spread of diseases.

16 Claims, 15 Drawing Sheets

(51) Int. Cl.
    *G01J 5/00*       (2022.01)
    *G16H 50/80*     (2018.01)

(58) Field of Classification Search
    CPC ........ G16H 50/20; G16H 50/30; G16H 30/40;
             G01J 5/026; G01J 5/025; G01J 5/0025;
             G01J 2005/0077; G08B 21/182; A61B
             5/01; A61B 5/00; A61B 2503/40; A61B
             5/746; A61B 5/4803; G06Q 50/02
    See application file for complete search history.

(56)                     References Cited

U.S. PATENT DOCUMENTS

| | | |
|---|---|---|
| 2018/0110416 A1 | 4/2018 | Masuda |
| 2019/0088271 A1 * | 3/2019 | Lee .......................... G10L 25/66 |
| 2019/0307106 A1 | 10/2019 | Hartung |

FOREIGN PATENT DOCUMENTS

| | | | | |
|---|---|---|---|---|
| KR | 101961311 B1 * | 7/2019 | ............... | A61B 5/01 |
| KR | 20200056820 A * | 5/2020 | ........... | A61B 5/7275 |
| KR | 102182737 | 11/2020 | | |
| NZ | 615942 A * | 10/2015 | ............. | G16H 50/20 |
| WO | WO-2014118788 A2 * | 8/2014 | ............. | G16H 40/67 |

* cited by examiner

FIG. 13A

SYSTEM FOR EARLY DETECTION OF INFECTIOUS DISEASES IN POULTRY

CROSS-REFERENCE TO RELATED APPLICATIONS

This application is a § 371 national stage entry of International Application No. PCT/KR2021/013984, filed on Oct. 12, 2021, which claims priority to Korean Patent Application No. 10-2020-0137664, filed on Oct. 22, 2020, the entire contents of which are incorporated herein by reference.

TECHNICAL FIELD

The present disclosure relates to a method for determining an overall health condition including outbreaks of a variety of poultry diseases by real-time measurement of quantitative change in vital signs including body temperature and noise level in poultry.

BACKGROUND ART

Infectious diseases of chicken reduce productivity in chicken farms, causing tremendous economic damage to the chicken industry. Among them, avian influenza infection is the disease which is caused by infection with influenza type A virus and spreads very quickly. In particular, infection with highly pathogenic avian influenza (HPAI) results in very high mortality in chicken, HPAI is designated as a Class 1 animal infectious disease in Korea. When infected with avian influenza, chickens show a variety of symptoms including loss of appetite, facial edema, respiratory distress, diarrhea, decreased egg production, cyanosis, etc. However, chickens infected with HPAI show rapidly increased mortality rate, in some cases up to 100%, in short time without any particular symptoms.

Intensive preemptive and post measures are being made to reduce economic loss caused by the HPAI. However, the infection spreads very quickly among chickens with few clinical symptoms, it is not easy to detect the infection in early phase and stop viral transmission. For this reason, early detection of avian influenza outbreak is very important and thus a large budget has been spent to that end. However, an efficient system for early detection of HPAI has not been developed yet.

Many articles and patent literatures are referred to and cited throughout the specification, and all citations are specified herein. The disclosures of the cited articles and patent literatures are incorporated in the specification by reference in their entirety to describe the present disclosure and the level of the technical field pertaining to the present disclosure more clearly.

RELATED LITERATURES

Patent Literature

Patent Literature 1. WO2016/170984.

DISCLOSURE

Technical Problem

The inventors have studied and made efforts consistently to develop a method for accurately determining an overall health condition including outbreaks of a variety of poultry diseases by measuring quantitative change of vital signs of poultry in real time. As a result, the inventors found that by comparing pre-measured values of body temperature and noise level of healthy poultry with body temperature and noise level of target poultry for the same time range, it is possible to correct errors based on circadian changes and thus to acquire information associated with vital signs of the poultry with higher reliability, and have completed the present disclosure.

Accordingly, the present disclosure is directed to providing a system for measuring changes in vital signs of poultry.

The present disclosure is further directed to providing a system for early prediction of pathogenic bacterial or viral infection in poultry.

These and other objectives and advantages of the present disclosure will become apparent from the following detailed description, the appended claims and the accompanying drawings.

Technical Solution

According to an aspect of the present disclosure, the present disclosure provides a system for measuring changes in vital signs of poultry, which includes:

a body temperature measurement unit which measures the body temperature of the poultry in a set unit of time through thermal imaging and transmits the measured values;

a noise measurement unit which measures the noise of the poultry in the set unit of time and transmits the measured values; and a server which receives the measured values transmitted from the body temperature measurement unit and the noise measurement unit, and sends an alert when an absolute value of a difference between the received measurement values and pre-measured body temperature and noise of the poultry for each time range is larger than a cut-off value.

The inventors have studied and made efforts consistently to develop a method for accurately determining an overall health condition including outbreaks of a variety of poultry diseases by measuring quantitative change of vital signs of poultry in real time. As a result, the inventors found that by comparing pre-measured values of body temperature and noise level of healthy poultry with body temperature and noise level of target poultry for the same time range, it is possible to correct errors caused by circadian changes and thus to acquire information associated with vital signs of the poultry with higher reliability, and have completed the present disclosure.

In the specification, the term "poultry" refers to birds domesticated or bred for human use, and specifically refers collectively to birds kept primarily for producing eggs, meat and feathers or birds kept as pets or for enjoyment. More specifically, the poultry to which the system of the present disclosure is applied is selected from the group consisting of chickens, ducks, geese, quails, pheasants and turkeys, and is most specifically chickens or ducks.

The body temperature measurement unit of the present disclosure provides thermal image information of the body temperature of the target poultry flock using a thermal camera as well as quantitative and numerical body temperature data in real time.

In the specification, the "set unit of time" refers to a length of time corresponding to a body temperature or noise measurement cycle. For example, when the unit of time is set to 30 minutes, 48 measurements and transmissions are performed over the course of a 24-hour circadian cycle. Specifically, the unit of time is 3 minutes to 15 minutes, more specifically 4 minutes to 10 minutes, and most specifically 5 minutes.

According to a particular embodiment of the present disclosure, the body temperature measurement unit measures and transmits the average, highest and lowest body temperature values of the poultry within the set unit of time.

According to a particular embodiment of the present disclosure, the noise measurement unit measures and transmits the average, highest and lowest noise values of the poultry in decibel (dB) units within the set unit of time.

The noise measurement unit of the present disclosure includes an audio collection unit to collect the sound made by the poultry using a single microphone or multiple microphones. The system of the present disclosure may further include an audio filter unit to extract the noise of the poultry by filtering out the surrounding noise from the collected audio information, and the audio filter unit may be included in the noise measurement unit, and may be included in the server that receives the data from the noise measurement unit. The audio filter unit may be connected wirelessly or via a cable to the audio collection unit to boost or reduce a specific frequency band of audio signals of the poultry through at least one filter of a high-pass filter, a low-pass filter or a jet noise filter in order to extract effective data.

According to a particular embodiment of the present disclosure, the pre-measured body temperature and noise of the poultry for each time range is selected from the group consisting of average, highest and lowest values of circadian changes pre-measured in a group of the same individuals or a group of individuals of the same species as the poultry for each time range and a combination thereof, and more specifically the average, highest and lowest values.

In the specification, the "circadian changes" refer to changes in the body temperature and noise level of the poultry in a 24-hour cycle. Based on the fact that there is a predetermined pattern of changes in the body temperature and noise level of poultry in a circadian cycle and there is a significant difference between the lowest and highest values in the pattern, the inventors measured the average, lowest or highest value for each set unit of time and compared it with the pre-measured body temperature/noise of normal individuals for the same time range. Through this, as opposed to simply comparing with the total daily average value, it is possible to significantly reduce errors and send alerts in real time immediately upon detecting abnormal conditions.

The measurement values of the normal individual (or the group of normal individuals) used as the cut-off value in the present disclosure may be pre-measured values of the same individuals to be measured, and may also be the values for different individuals that belong to the same species pre-measured under the same or similar conditions. In any case, the measurement is performed on normal individuals that do not have poultry diseases affecting their vital signs.

According to a particular embodiment of the present disclosure, the measurement of the circadian change values is performed under light stimulation at a 12-hour interval.

The light stimulation may be performed by repeating exposure and interruption of natural light in a 12-hour cycle, and may be performed by repeatedly turning on and off artificial light.

According to a particular embodiment of the present disclosure, the cut-off value for the body temperature is 0.7 to 2° C., more specifically 0.8 to 1.8° C., and most specifically 0.8 to 1.6° C.

According to a particular embodiment of the present disclosure, the cut-off value for the noise is 4 to 8 dB, more specifically 5 to 7 dB, and most specifically 5 to 6 dB.

Specifically, the difference between the measurement value for each time range and the pre-measured value in the same time range may be derived by comparing at least one value of the highest value, the lowest value or the average value of the corresponding time range.

According to the present disclosure, when the absolute value of the difference between the highest value, the lowest value or the average value of body temperature and noise of the target poultry within the unit of time and the pre-measured value of a normal poultry (group) used as a control group is larger than the above-described cut-off value, it is determined that abnormality occurred in the vital signs of the target poultry. The server of the system of the present disclosure may be set to issue an alert when all the lowest value difference, the highest value difference and the average value difference within the set unit of time are larger than the cut-off value, may be set to issue an alert when one of these values is larger than the cut-off value, or may be set to issue an alert when two of these values are larger than the cut-off value.

According to a particular embodiment of the present disclosure, the system further includes a service system which provides server data including a real-time measurement value, a measurement history and an alert sending history.

The service system of the present disclosure may include a WEB system and a mobile APP. For example, search may be conducted to find real-time data of a test farm in which the poultry is raised and related statistics including the measurement history and the alert sending history through user's log-in on WEB and APP. Specifically, it may be designed such that the information of the test farm, setting of the unit of time for measurement and alert sending requirement setting are available in the WEB system only by a system manager.

According to another aspect of the present disclosure, the present disclosure provides a system for early prediction of pathogen infection in poultry including the above-described system of the present disclosure.

In the specification, the "early prediction" refers to determination of the risk of suspected pathogen infection through direct or indirect markers of infection before pathogen infection is diagnosed clinically. The individual (or the group of individuals) to which alert has been sent by the system of the present disclosure may be clinically diagnosed with an infectious disease or may be determined to be not yet infected through genetic testing, etc. Accordingly, the present disclosure is directed to providing an animal disease control system for identifying suspected infection with highly infectious pathogen such as avian influenza virus and efficiently stopping the spread of diseases through preemptive measures such as early isolation.

According to a particular embodiment of the present disclosure, the pathogen is a pathogenic bacterium or virus, and more specifically, a pathogenic bacterium or virus causing a measurable body temperature rise. More specifically, the virus is avian influenza virus, more specifically H5 avian influenza virus, and most specifically H5N6 avian influenza virus.

According to still another aspect of the present disclosure, the present disclosure provides a method for predicting pathogen infection in poultry, including the steps of:

measuring the body temperature, noise or a combination thereof of the poultry in a set unit of time;

deriving a difference value between the measurement value and pre-measured body temperature, noise or a combination thereof of the poultry for each time range or a combination thereof, and determining that the poultry is infected with a pathogen when the absolute value of the difference value is larger than a cut-off value.

The poultry, the pathogen, the cut-off value, etc. used in the present disclosure have been already described above, and their description is omitted to avoid unnecessary redundancy.

Advantageous Effects

The features and advantages of the present disclosure are summarized as follows:

(a) The present disclosure provides a system for measuring changes in vital signs of poultry and a method for predicting pathogen infection in poultry using the same.

(b) The present disclosure may be usefully used to determine an overall health condition including outbreaks of a variety of poultry diseases by measuring quantitative change of vital signs of poultry in real time.

(c) The present disclosure may be used especially in an efficient animal control system that provides real-time information of changes in vital signs with higher reliability through comparison for each time range reflecting circadian changes of poultry, instead of simply comparing the body temperature and noise measurement values of poultry with a single reference value, thereby achieving early diagnosis of highly infectious pathogens such as avian influenza virus and early isolation of confirmed cases, and ultimately stopping the spread of diseases.

DESCRIPTION OF DRAWINGS

FIGS. 13A and 13B schematically show a service area of a system for early detection of highly pathogenic avian

Figure 13A:
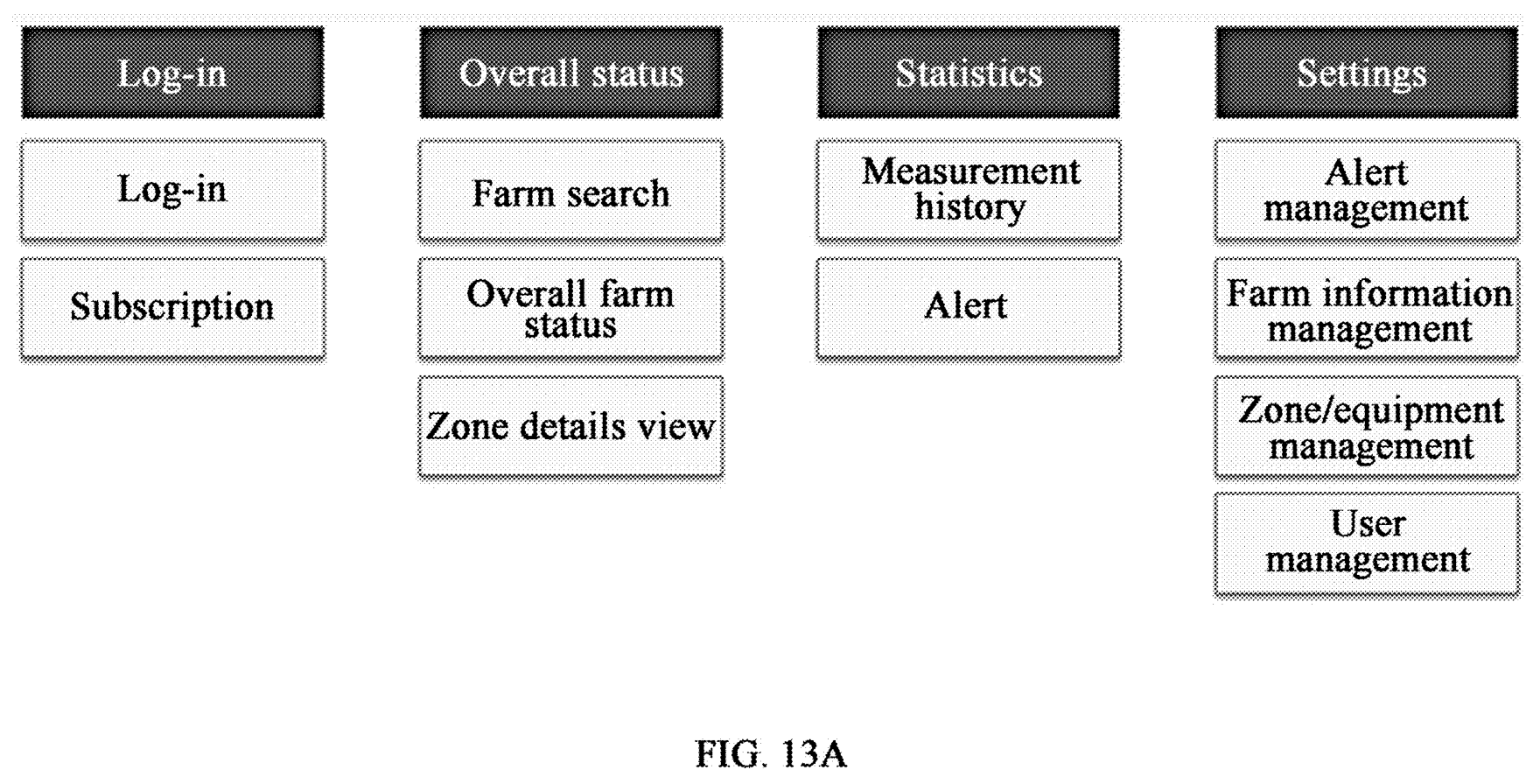
Figure 13B:
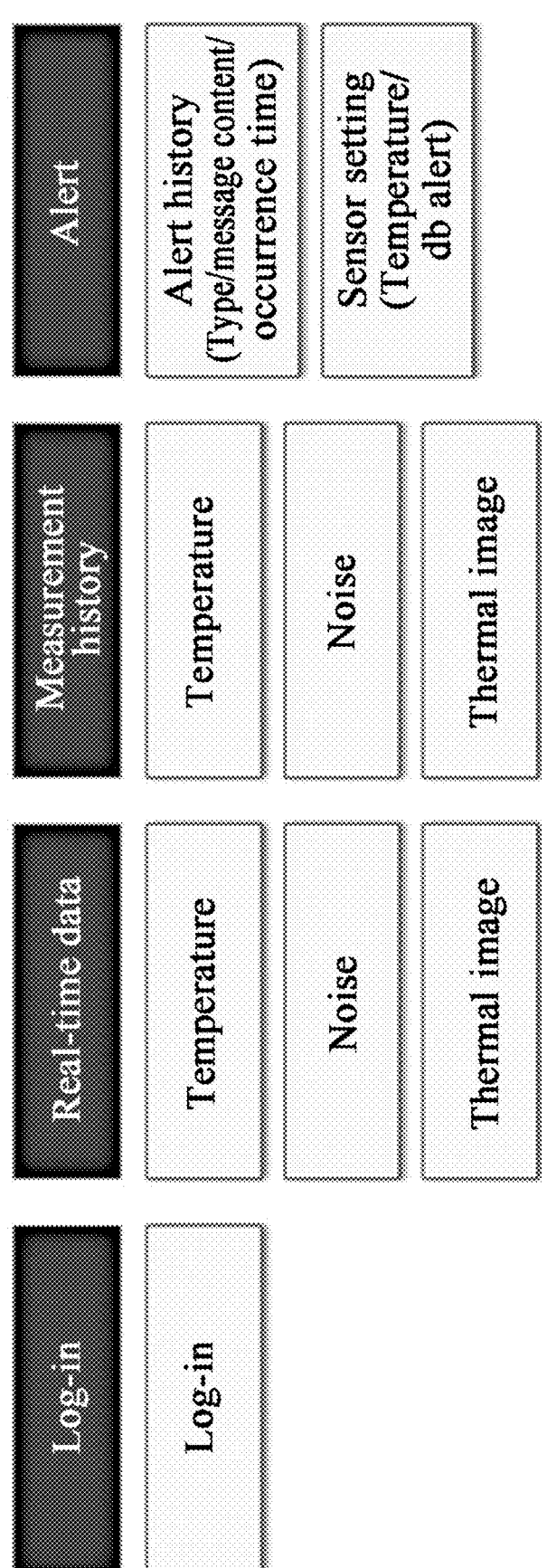

6 influenza of the present disclosure, exemplifying a WEB system menu (FIG. 13A) and an APP system menu (FIG. 13B).

BEST MODE

Hereinafter, the present disclosure will be described in more detail through examples. These examples are provided to describe the present disclosure in more detail, and it will be obvious to those skilled in the art that the scope of the present disclosure is not limited by the examples according to the subject matter of the present disclosure.

EXAMPLES

Example 1: Real-Time Monitoring of Fever Caused by Infection

Acquisition of Highly Pathogenic Avian Influenza Virus

Highly pathogenic avian influenza H5N6 A/duck/Korea/ES2/2016 virus (Accession number: KVCC VR160038) was introduced into 9- to 11-day-old SPF eggs and cultivated at 37° C. for 72 hours. Eggs that died within 24 hours during the cultivation period were determined to have died of the vaccination and discarded. The remaining eggs were stored at 4° C. for 3 hours and the proliferated virus was collected.

Fever Measurement of Chickens in Laboratory Using Thermal Camera

Five 6-week-old SPF chickens were isolated in a Biosafety Level 3 (BL3) cage and inoculated with highly pathogenic avian influenza H5N6 A/duck/Korea/ES2/2016 virus at the dose of $10^{6.0}$ $EID_{50}$ per bird (IACUC registration number KU18193). Subsequently, symptoms and mortality were measured on a daily basis, and changes in body temperature were monitored using a thermal camera. Additionally, to determine if the inoculation with the virus was carried out successfully, the release or discharge of the virus was measured by RT-PCR in real time for oropharyngeal and cloacal samples taken 2 days after the inoculation.

Figure 1:
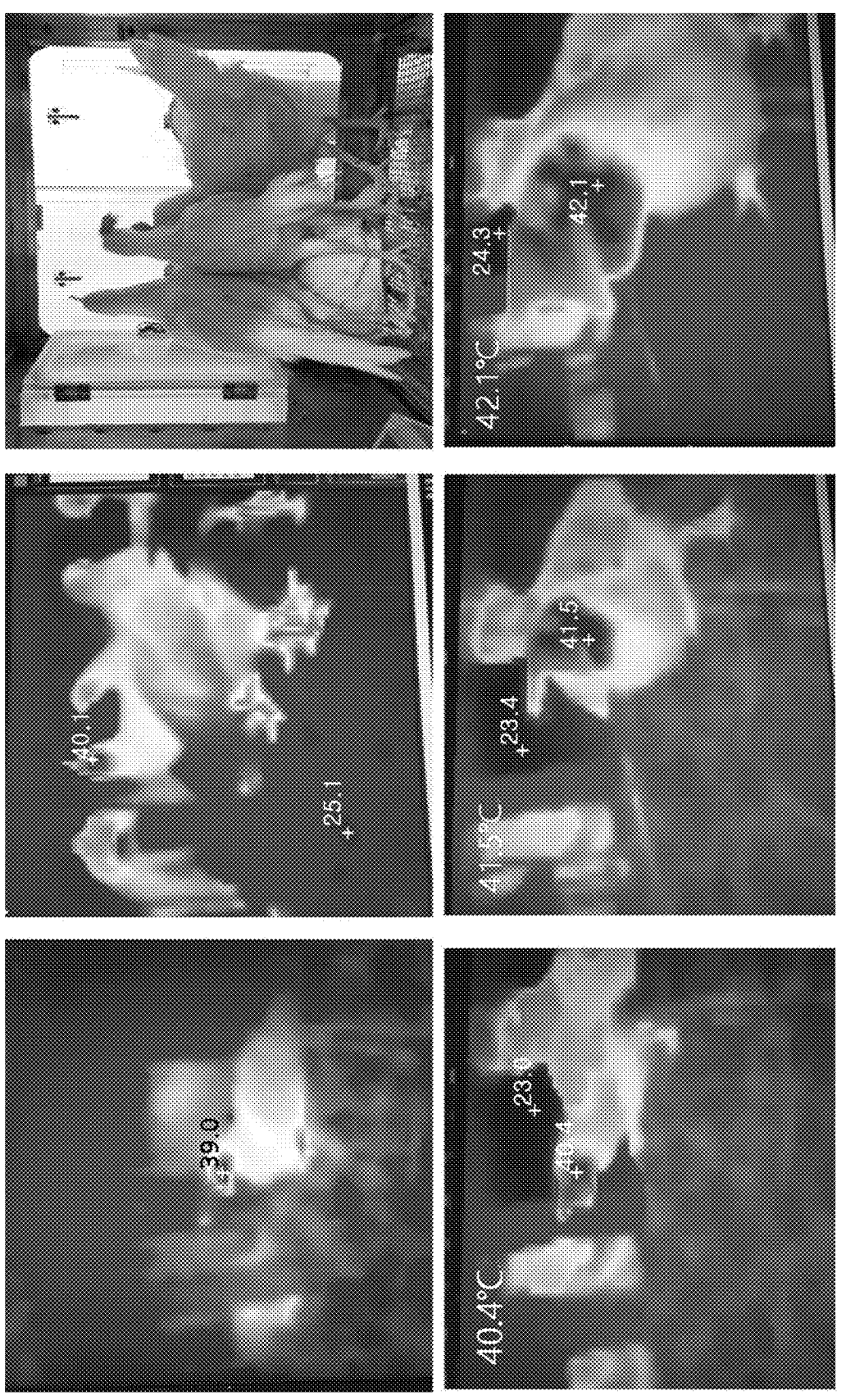
FIG. 1 shows a result of body temperature measurement of a test group before infection using a thermal camera.
Figure 2:
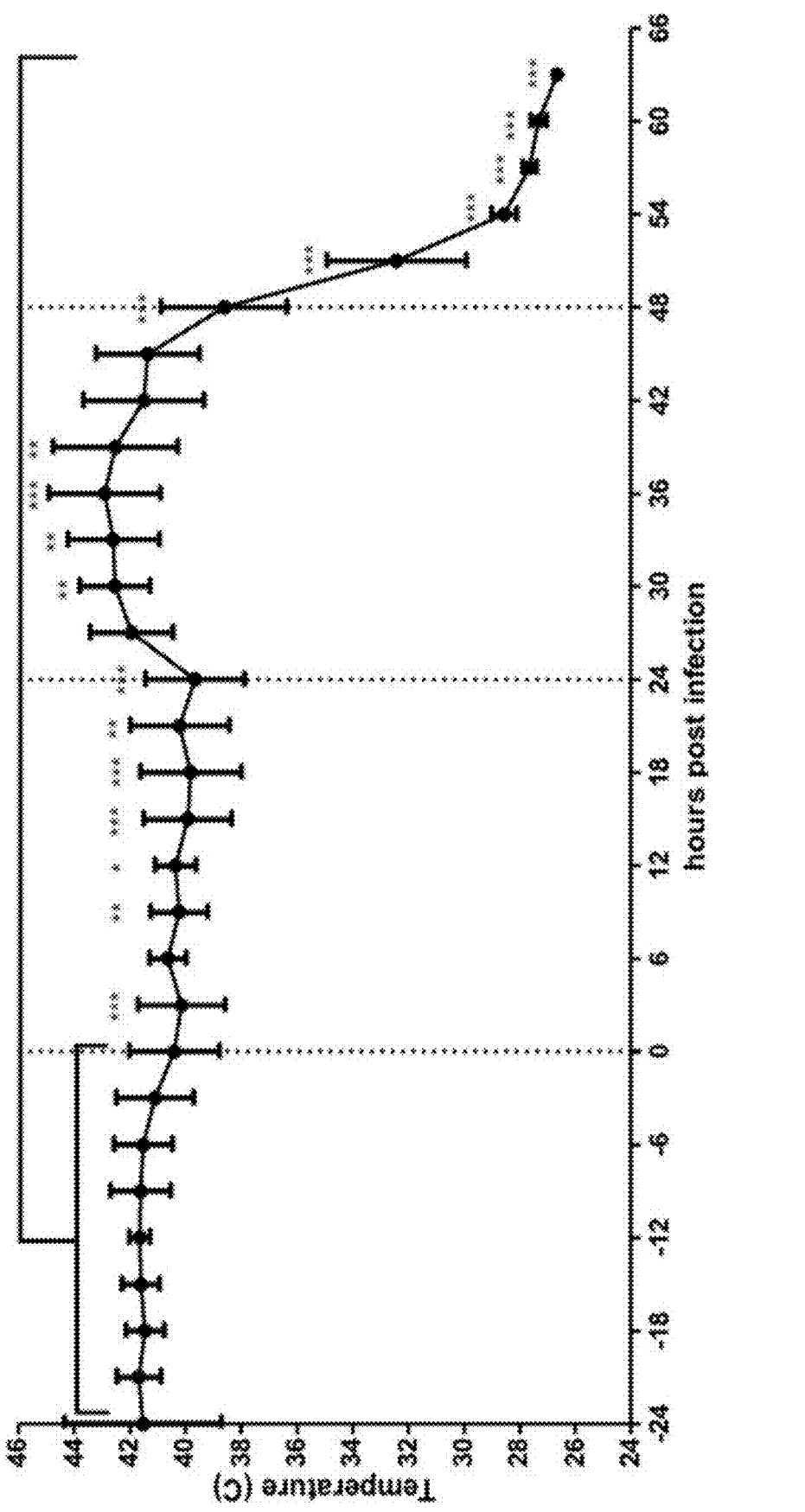
FIG. 2 shows a result of measuring average body temperature changes of each individual during a test period from 24 hours before infection to 66 hours after infection.

As a result of the test, the average body temperature before the highly pathogenic avian influenza infection was 40.5 to 42.4° C. (FIG. 2), and the highest body temperature was observed at the heads and legs regardless of infection (FIG. 1). The body temperature started to rise from 20 hours after the highly pathogenic avian influenza virus infection, showed the highest body temperature rise of about 2° C. at 27 to 36 hours, and subsequently, started to drop, and the chickens showed lack of strength and died within 44 hours. The virus was detected in all the oropharyngeal and cloacal samples taken 2 days after the infection.

Fever Measurement of Ducks in Laboratory Using Thermal Camera

Eighteen 5-week-old ducks were grouped into 3 groups and isolated in a Biosafety Level 3 (BL3) cage (IACUC registration number KU18193). The first and second groups were respectively inoculated with highly pathogenic avian influenza virus at the dose of $10^{4.0}$ $EID_{50}$ and $10^{8.0}$ $EID_{50}$ per bird through the nasal passage, and the third group, a negative control group, was injected with the same amount of PBS (Table 1). After the inoculation, symptoms and mortality were measured on a daily basis, and body temperature changes for 14 days were measured using a thermal camera. Additionally, to determine if the inoculation with virus was carried out successfully, the release or discharge of the virus was measured in real time for oropharyngeal and cloacal samples by RT-PCR.

US 12,667,084 B2

7

TABLE 1

| Species | Age | Number of animals | Infectious dose |
|---|---|---|---|
| Duck | 5-week old | 6 | Highly pathogenic avian influenza $10^{4.0}$ $EID_{50}$/per bird |
| Duck | 5-week old | 6 | Highly pathogenic avian influenza $10^{8.0}$ $EID_{50}$/per bird |
| Duck | 5-week old | 6 | PBS |

Figure 3:
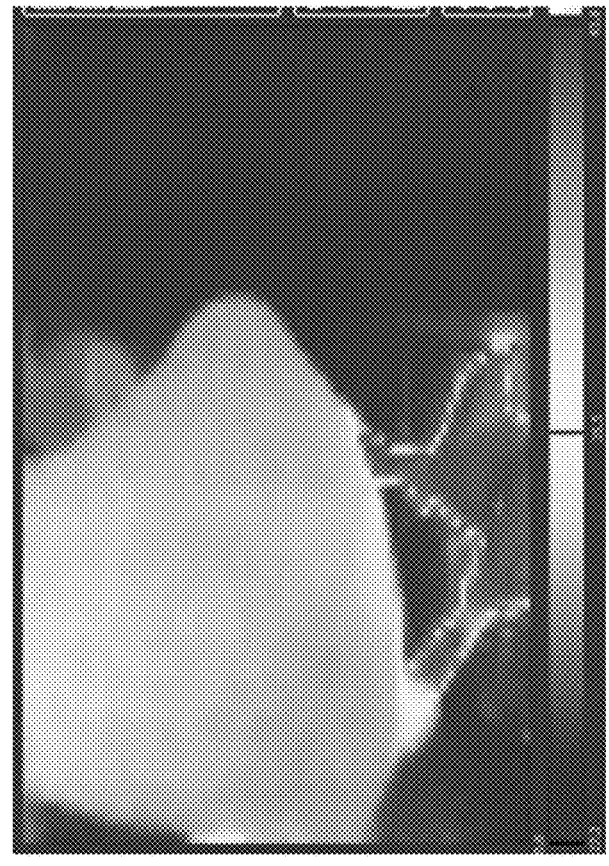
FIG. 3 shows a result of body temperature measurement of a test group before infection using a thermal camera.
Figure 3:
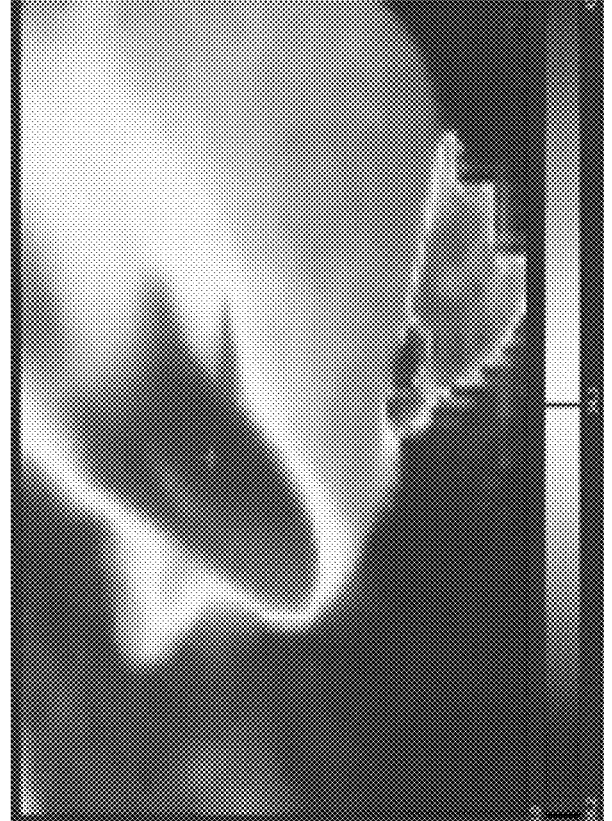
Figure 4:
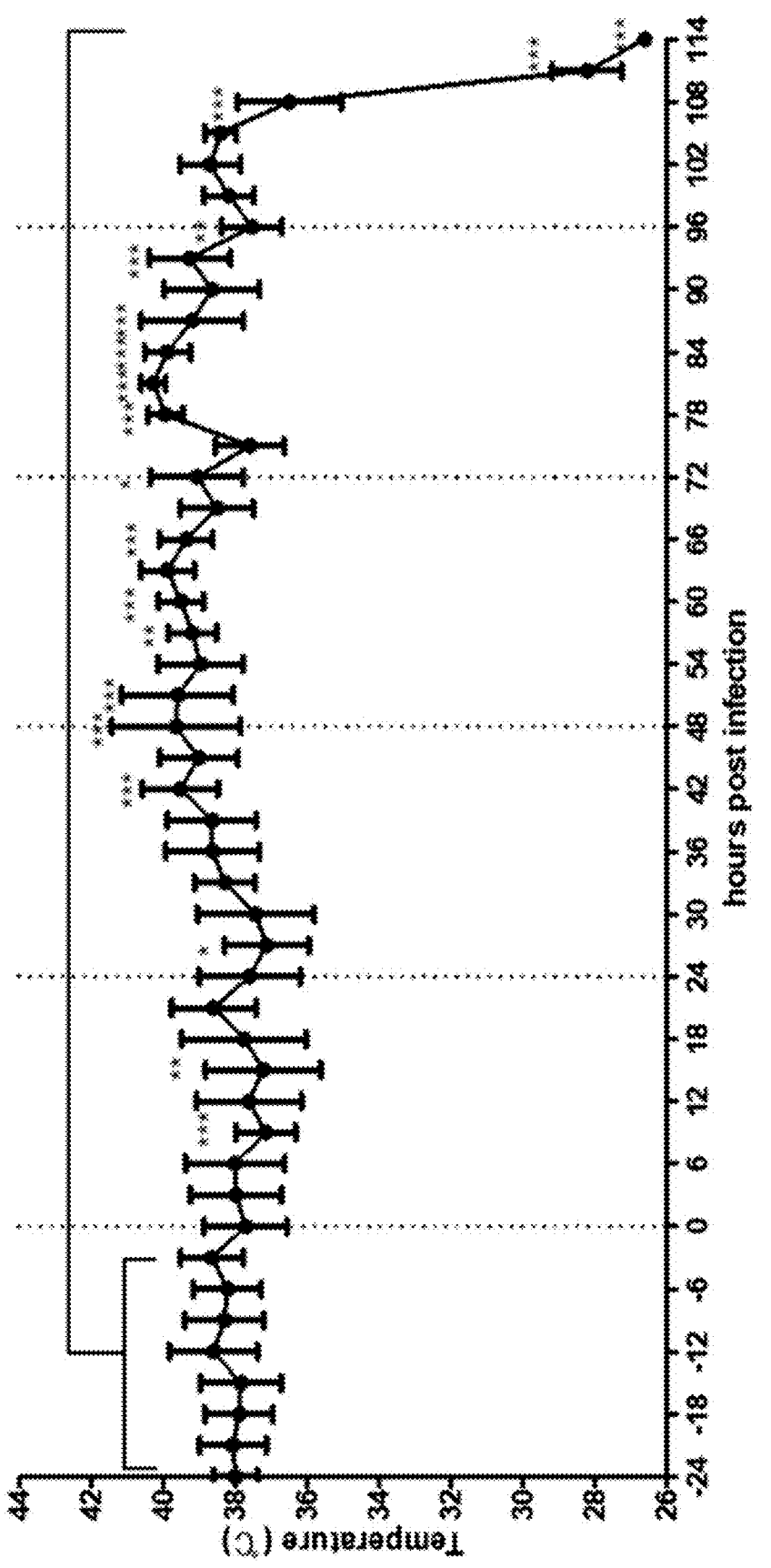
FIG. 4 shows a result of measuring average body temperature changes of individuals that have died of infection.
Figure 5:
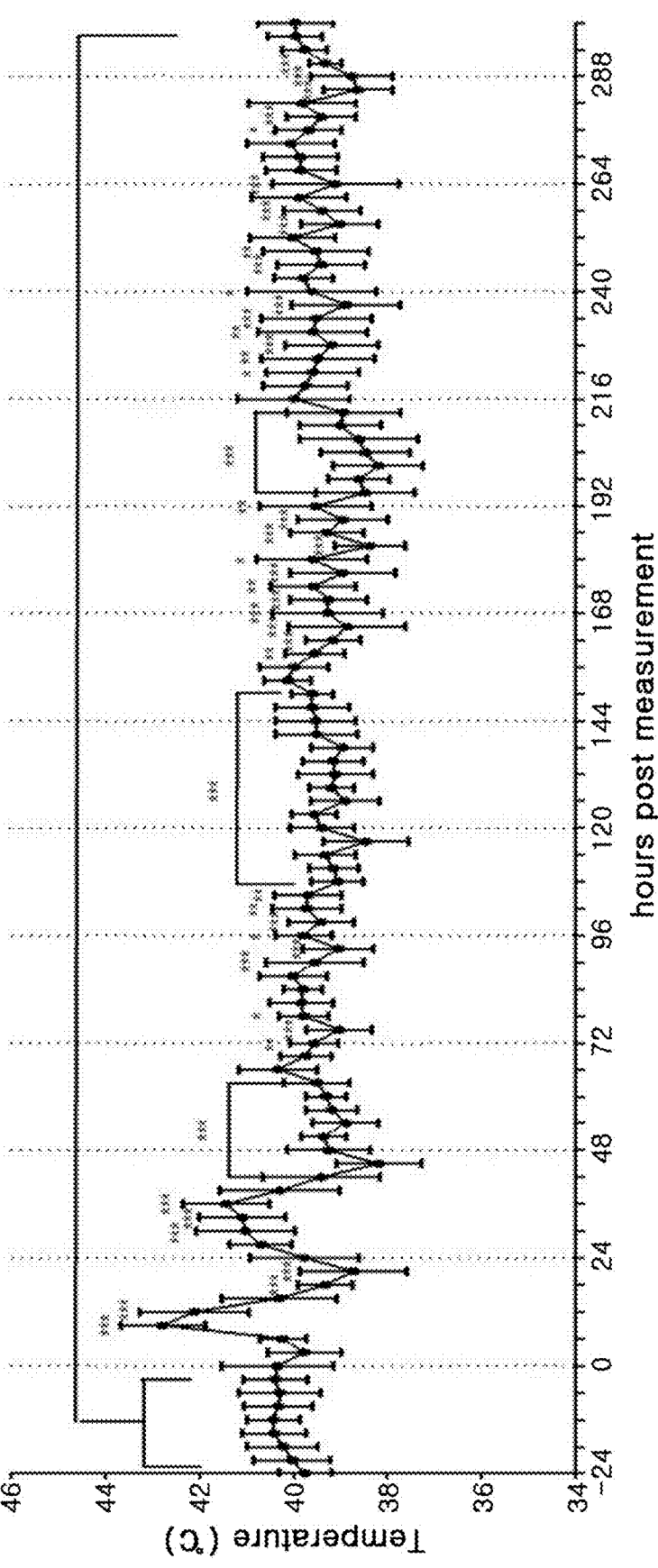
FIG. 5 shows a result of measuring average body temperature changes of individuals that have survived after infection.

As a result of the test, the average body temperature before the highly pathogenic avian influenza infection was 38.2 to 42.0° C., and the highest body temperature was observed from the beaks, wings and legs regardless of infection (FIG. 3). After the vaccination, in the test group inoculated with the virus at the dose of $10^{8.0}$ $EID_{50}$ per bird, 3 out of 6 ducks died, and these individuals showed the similar body temperature rise to the chickens but a lower rise rate than the chickens (FIG. 4). Additionally, there were no specific symptoms until immediately before death. Generally, the body temperature started to rise from 40 hours after the vaccination and showed the highest body temperature rise of about 1.1° C. at 80 to 86 hours. In contrast, significant body temperature change was not observed in the surviving individuals during the test period (FIG. 5), but highly pathogenic avian influenza virus was detected, and thus asymptomatic infection was confirmed.

Example 2: Real-Time Monitoring of Average Biological Rhythm of Chickens

Real-Time Circadian Changes of Average Body Temperature and Noise on Small Scale Floor Thirty 1-day-old broiler chickens were raised on 2 m×2 m floor and a brooder was used in the early stage to maintain proper body temperature. From 13 days, light stimulation was performed at a 12-hour interval and circadian rhythms were observed using a thermal camera and a noise meter.

Figure 6:
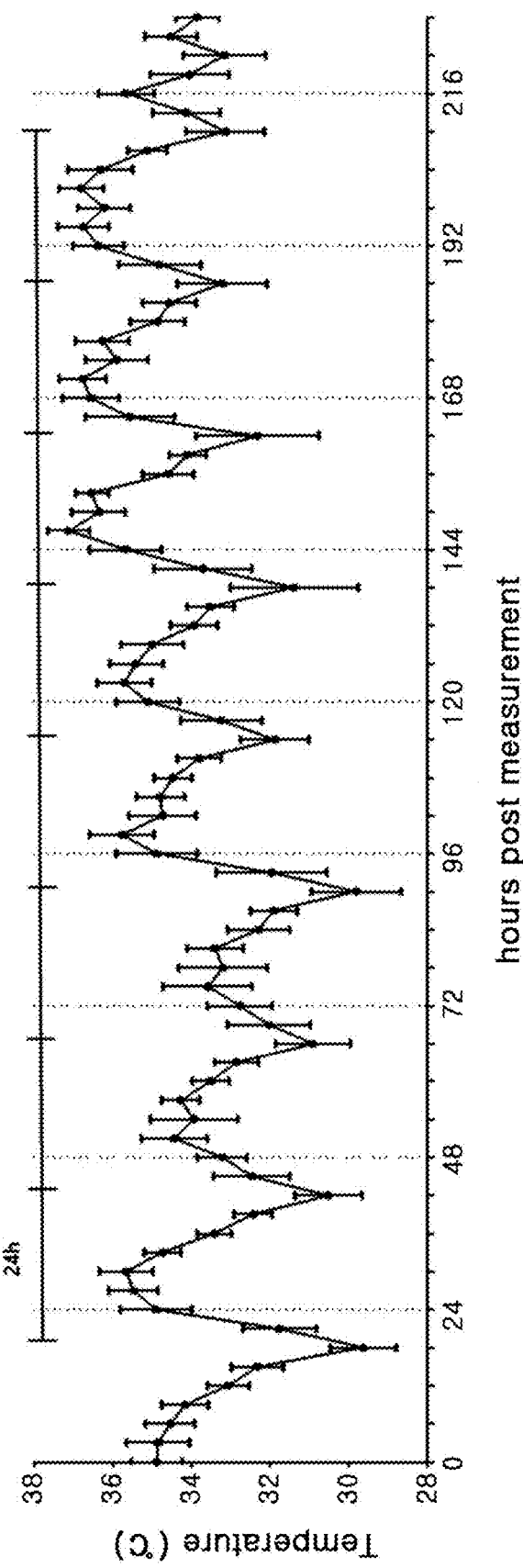
FIGS. 6 and 7 respectively show results of measuring average body temperature changes (FIG. 6) and average noise changes (FIG. 7) from day 13 after raising 30 broiler chickens on a floor of 2 m×2 m in size.
Figure 7:
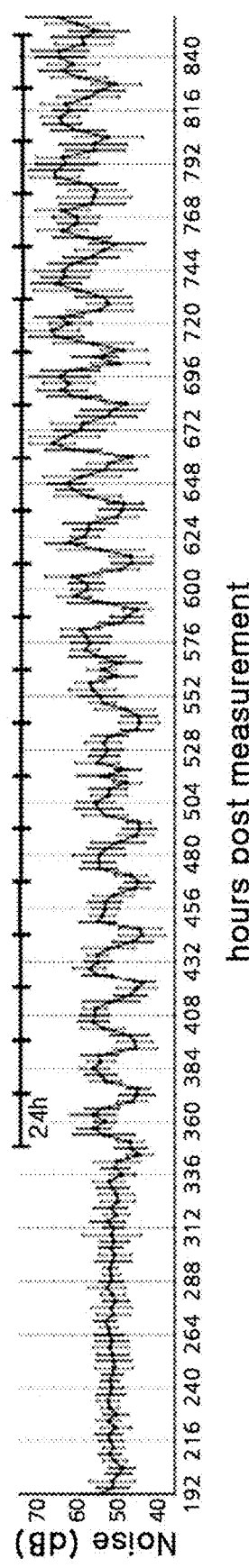
Figure 8:
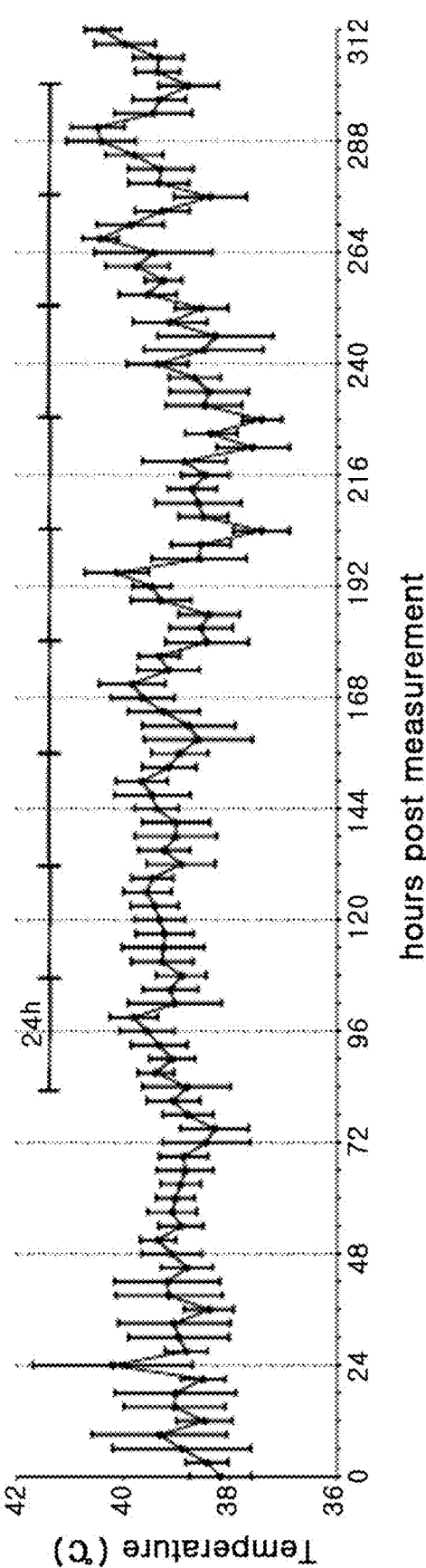
FIGS. 8 and 9 respectively show first (FIG. 8) and second (FIG. 9) measurement results of average body temperature changes of broiler chickens being actually raised in a farm.
Figure 9:
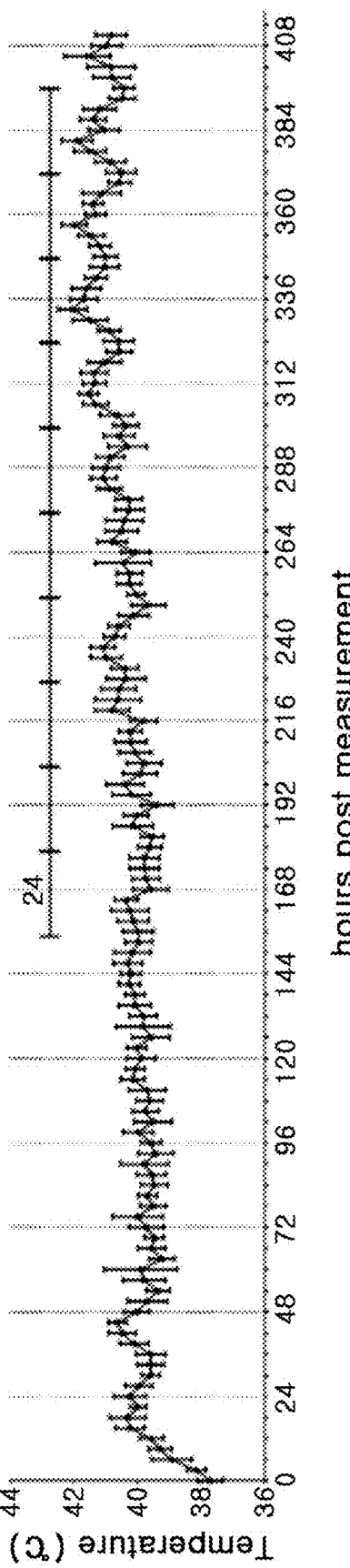
Figure 10:
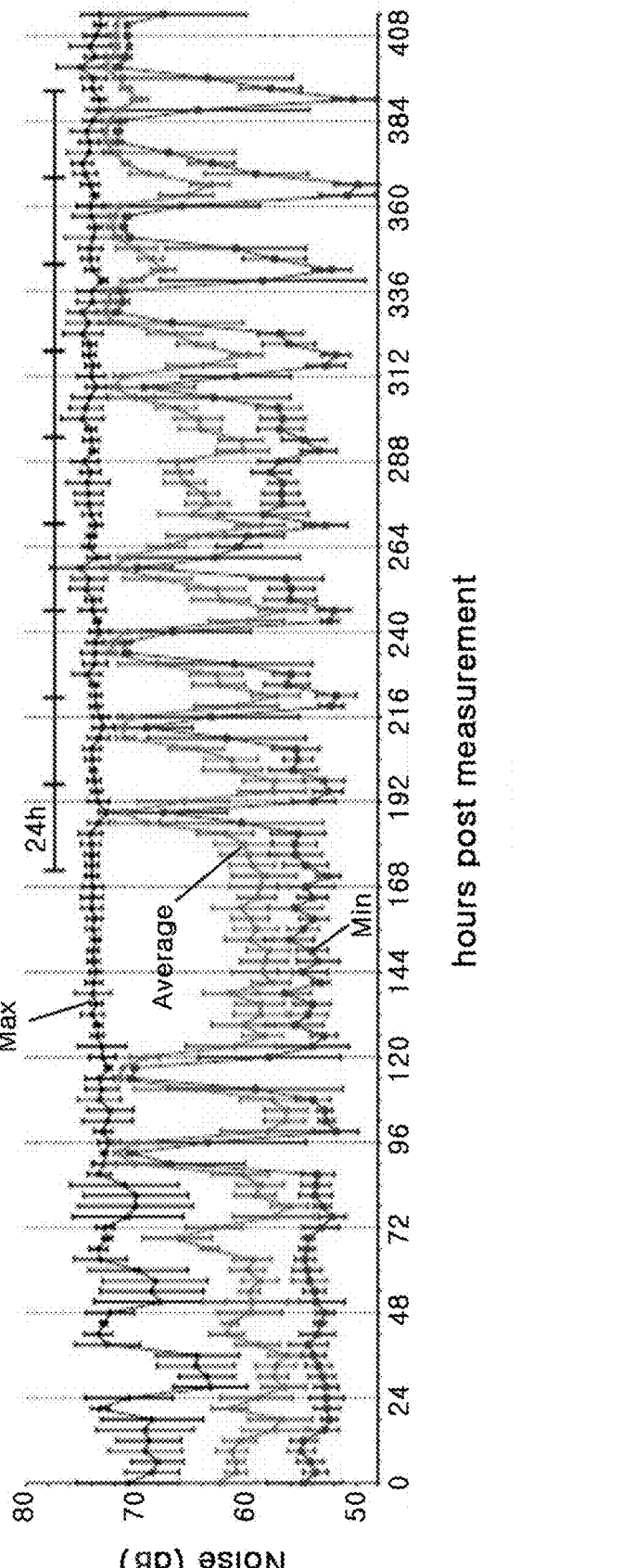
FIGS. 10 and 11 respectively show first (FIG. 10) and second (FIG. 11) measurement results of average noise changes of broiler chickens being actually raised in a farm.
Figure 11:
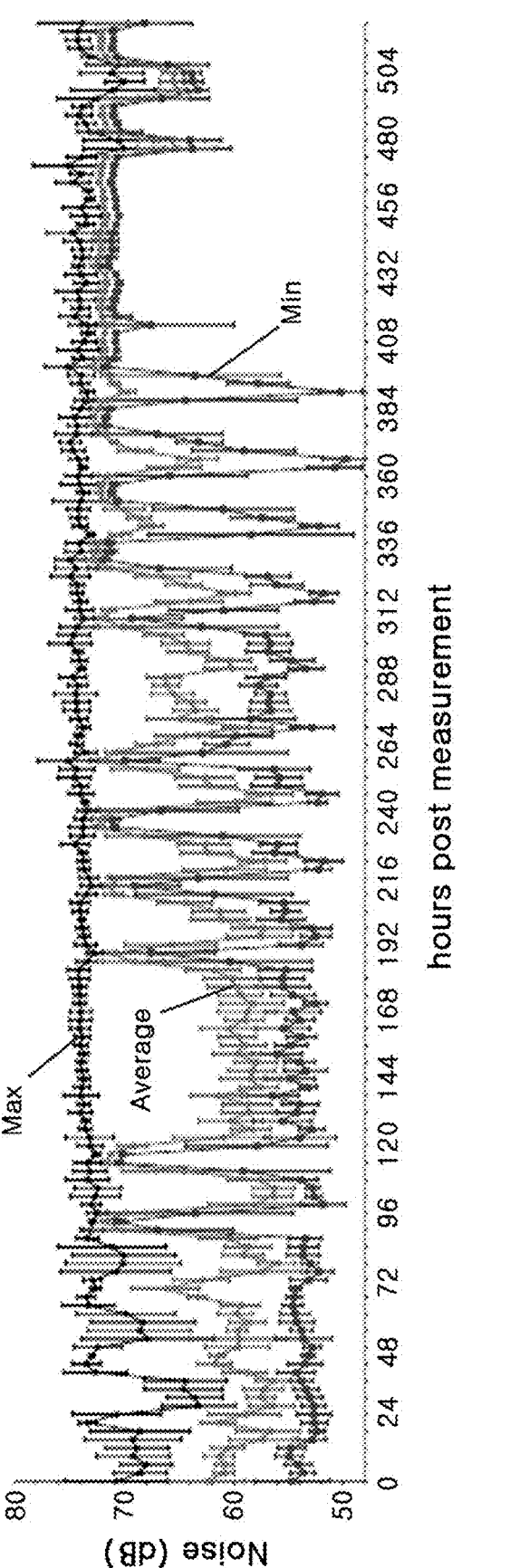

As a result of the test, the body temperature showed a pattern of changes at a regular interval (FIG. 6), and it was confirmed that it was possible to detect abnormal body temperature of the chickens for each time range more accurately, thereby reducing the frequency of error. In the case of noise, while lights were turned on, the chickens were very active and the measurement value was high. On the contrary, while lights were turned off, the measurement value tended to decrease. With the growth of the chickens, a generally increasing pattern of noise was exhibited. Through this, it is thought that it will be possible to determine abnormal conditions of the chickens more accurately based on the generally decreasing tendency of noise measurement values since the chickens are less active when infected.

Real-Time Tracking of Circadian Changes of Average Body Temperature and Noise in Actual Broiler Chicken Farm Imaging noise measurement were performed on broiler chickens two times from entry at the first day to exit using a thermal camera and a noise meter in a line of floor space of the farm in which the chickens were actually raised.

As a result of the test, a predetermined pattern of changes in body temperature could be seen, and thus it was possible to detect abnormal body temperature of the chickens for each time range more accurately, thereby reducing the frequency of error. Furthermore, it may be usefully applied to identify highly pathogenic avian influenza infection as well as the condition of the chickens more accurately according to the raising environment of the farm and season, such as the use of antipyretics to reduce fever caused by vaccination, etc. Also, in the case of noise, it showed a periodic pattern on average, and light on/off and measurement of the total vitality level of the chickens could be performed based on the pattern.

Alarming System for Notifying Abnormal Fever and Noise

Figure 12A:
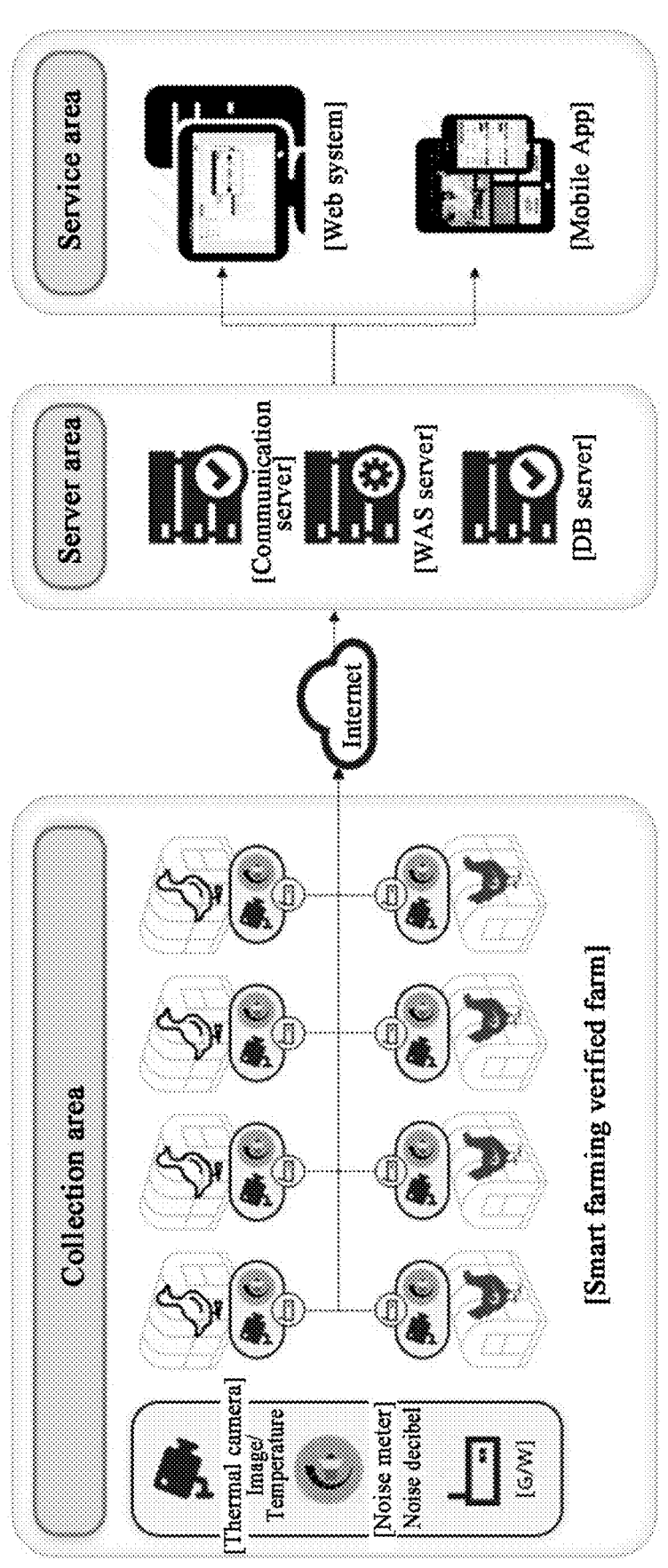
FIGS. 12A and 12B schematically show a system for early detection of highly pathogenic avian influenza of the present disclosure (FIG. 12A) and the hardware and software components of a server area (FIG. 12B).

A prototype system was developed for the purpose of early detection of highly pathogenic avian influenza through identification of changes in the vital signs of poultry. The system includes three areas, a data collection area, a server area and a service area, and the data collected on the spot is transmitted to the server via the Internet (FIG. 12A).

The data collection area was selected as a site in which a predetermined number of broiler chicken individuals were observed in a test smart farm, and a thermal camera and a noise measurement device were installed there. The thermal camera measures temperature data for 6,400 pixels (80×80) every 5 minutes (a set cycle), and through this, average/highest/lowest temperature values and images are received in each set cycle. The noise measurement device is set to the same measurement/transmission cycle as the thermal camera to receive average/highest/lowest decibel (dB) data every 5 minutes.

Figure 12B:

The server area includes a communication server, a WAS server and a DB server (FIG. 12B). The communication server takes responsibility for each communication system (G/W) of the thermal camera and the noise measurement device installed at the test farm, and the data collected by the WAS server are processed and are finally stored in the DB server.

The service area includes a WEB system and a mobile APP (FIG. 13). The WEB system and the mobile APP are designed to have the same main functions to search real-time data of the test farm and search for measurement history and alert statistics through user's log-in on WEB and APP, but a system environment setting sector (farm information/zone/equipment/user management) is only available in the WEB system, in consideration of user UI/UX.

1) Example of Main Functions of WEB System

Overall status: farm search (name, address), overall farm status search, details view per zone Statistics: measurement history for each terminal, alert history, report output Settings: alert requirement setting for each time range, farm information/zone/equipment/user management 2) Main Functions of APP System Real-time data: real-time measurement value (temperature, noise, thermal image) search for each terminal Measurement history: measurement history for each terminal Alert: alert history, lowest/highest alert value setting for each time range Specific exemplary embodiments of the present disclosure have been described hereinabove in detail, but they are only exemplary embodiments. Accordingly, it is obvious to those having ordinary knowledge in the art that the scope of the present disclosure is not limited thereto. Accordingly, the substantial scope of the present disclosure will be defined by the appended claims and their equivalent.

The invention claimed is:

1. A system for measuring changes in the vital signs of poultry, comprising:

a body temperature measurement unit configured to measure body temperature of the poultry in a set unit of time through thermal imaging and transmit the measurement value;

a noise measurement unit configured to measure noise of the poultry in the set unit of time and transmit the measurement value; and a server configured to receive the measurement values transmitted from the body temperature measurement unit and the noise measurement unit, and send an alert when the absolute value of a difference between the received measurement values and pre-measured body temperature and noise of the poultry for each time period is larger than a cut-off value;

wherein the pre-measured body temperature and noise of the poultry for each time period are values of normal circadian changes over time which are pre-measured in a group of the same individuals or in a group of individuals of the same species as the poultry for each time period.

2. The system according to claim 1, wherein the body temperature measurement unit is configured to measure and transmit average, highest and lowest body temperature values of the poultry within the set unit of time.

3. The system according to claim 1, wherein the noise measurement unit is configured to measure and transmit average, highest and lowest noise values of the poultry in decibel (dB) units within the set unit of time.

4. The system according to claim 1, wherein the pre-measured body temperature and noise of the poultry for each time range are selected from the group consisting of average, highest and lowest values and a combination thereof of circadian changes pre-measured in a group of the same individuals or a group of individuals of the same species as the poultry for each time range.

5. The system according to claim 1, wherein the unit of time is 3 minutes to 15 minutes.

6. The system according to claim 1, wherein the cut-off value for the body temperature is 0.7° C. to 2° C.

7. The system according to claim 1, wherein the cut-off value for the noise is 4 dB to 8 dB.

8. The system according to claim 1, further comprising:
a service system configured to provide server data including a real-time measurement value, a measurement history and an alert sending history.

9. The system according to claim 1, wherein the poultry is selected from the group consisting of chickens, ducks, geese, quails, pheasants and turkeys.

10. A system for early prediction of pathogen infection in poultry comprising the system according to claim 1.

11. The system according to claim 10, wherein the pathogen is a pathogenic bacterium or virus causing a measurable body temperature rise.

12. The system according to claim 11, wherein the virus is avian influenza virus.

13. A method for predicting pathogen infection in poultry, comprising the steps of:
measuring the body temperature, noise or a combination thereof of the poultry in a set unit of time;

deriving a difference value between the measurement value and pre-measured body temperature, noise or a combination thereof of the poultry for each time period or a combination thereof; and predicting that the poultry is infected with a pathogen when the absolute value of the difference value is larger than a cut-off value;

wherein the pre-measured body temperature, noise or a combination thereof of the poultry for each time period are values of normal circadian changes over time which are pre-measured in a group of the same individuals or in a group of individuals of the same species as the poultry for each time period.

14. The method according to claim 13, wherein the poultry is selected from the group consisting of chickens, ducks, geese, pheasants and turkeys.

15. The method according to claim 13, wherein the pathogen is a pathogenic bacterium or virus causing a measurable body temperature rise.

16. The method according to claim 15, wherein the virus is avian influenza virus.

* * * * *